(12) United States Patent
O'Lenick, Jr. et al.

(10) Patent No.: US 7,132,558 B1
(45) Date of Patent: Nov. 7, 2006

(54) SILICONE VITAMIN ESTERS

(75) Inventors: Anthony J. O'Lenick, Jr., Dacula, GA (US); Thomas G. O'Lenick, Dacula, GA (US)

(73) Assignee: SurfaTech Corporation, Dacula, GA (US)

( * ) Notice: Subject to any disclaimer, the term of this patent is extended or adjusted under 35 U.S.C. 154(b) by 139 days.

(21) Appl. No.: 10/776,693

(22) Filed: Feb. 12, 2004

(51) Int. Cl.
*C07F 7/08* (2006.01)

(52) U.S. Cl. ........................ 556/456; 556/440; 556/437

(58) Field of Classification Search ................ 556/456, 556/437, 440
See application file for complete search history.

(56) References Cited

U.S. PATENT DOCUMENTS 5,210,133 A    5/1993    O'Lenick et al.

*Primary Examiner*—Samuel Barts

(57) ABSTRACT

The invention discloses novel series of silicone esters, which are useful as antioxidants on skin. The products are produced using for a variety of hydroxyl containing actives such as vitamin A (retinol), vitamin A-2, and vitamin E. Compounds of the invention are prepared by the esterification of (a) a specific silicone methyl ester and (c) a hydroxyl functional active. The esters of the present invention allow for the formulation of personal care products in which the "active" can be formulated into a variety of solvents without the loss of activity.

16 Claims, No Drawings

SILICONE VITAMIN ESTERS

BACKGROUND OF THE INVENTION

1. Field of the Invention

The invention discloses novel series of silicone esters which are useful as antioxidants on skin. The products are produced using for a variety of hydroxyl containing actives such as vitamin A (retinol), vitamin A-2, and vitamin E. Compounds of the invention are prepared by the esterification of (a) a specific silicone methyl ester and (c) a hydroxyl functional active. The esters of the present invention allow for the formulation of personal care products in which the "active" can be formulated into a variety of solvents without the loss of activity.

By hydroxyl, functional active is meant a vitamin, co-vitamin, or other material known to effect a change to the hair or skin, which contains a hydroxyl group or hydroxyl groups.

2. Arts and Practices

The personal care market is a very diverse market segment, which includes a number of products designed to protect the skin and hair from the degradation effects of sunlight and environmental distress caused by free radicals.

In addition to protecting the hair and skin by acting as antioxidants, there is a need for products that improve the condition of the hair, skin nails, and lips. The desirable functions include but are not limited to; barrier properties, remoisturization, softening, and conditioning.

One of the most important functions of human skin is the protection against adverse environmental factors. Environmental factors like exposure of the skin to sun, cold or heat adversely affects the skin and minimizes the barrier property of the skin. Additionally, the application of many cosmetic products or use of soap on the skin removes the fatty layer of the skin. It is therefore highly desirable to replace the barrier properties, which are removed from the skin. Lipids and other oily materials added to the skin improve the natural barrier properties of the skin and hair the skin retain moisture and feel soft. If a suitable delivery system is used Vitamin A, Vitamin A-2, and Vitamin E are excellent materials for use as moisturizing and barrier créme applications. These materials are very difficult to deliver from aqueous environment. One attempt to deliver these materials to the skin has been to make emulsions of these oils in water. This is done by selecting surface-active agents, which will emulsify the hydroxyl active into small droplets, which are surrounded by the surface-active agent in what are called micelles. The resulting emulsion resembles milk and contains the emulsified hydroxyl active. The difficulty with this approach is that the material present in the micelle is deposited very inefficiently onto the hair and skin since the micelle must break to deliver the oil. Since the majority of the micelles do not break, the majority of the active is rinsed off and ends up in the drain. Another approach has been to make derivatives of these oily materials. There has therefore been a long felt need for materials, which could be incorporated into personal care products, which deliver vitamins to the skin.

We have discovered that the incorporation of Vitamin A, Vitamin A-2, and Vitamin E, into a silicone ester in relatively low concentrations results in polyesters which can be made soluble in many different solvents and which give the beneficial properties of the cholesterol or lanolin to the skin and hair. In short, low concentrations of these esters by virtue of their substantivity to hair and skin will provide outstanding protection from oxidation and free radical attack as well as moisturizing properties in many varied personal care formulations. Activity is seen at as low as 0.1%.

U.S. Pat. No. 5,210,133 to O'Lenick Jr., issued May 1993 discloses "novel series of silicone polyesters which are useful as delivery systems for a variety of hydroxyl containing active such as lanolin, cholesterol, dihydrocholesterol, Vitamin A, Vitamin D-2, Vitamin D-3, Vitamin D-4, Vitamin E, and panthenol.

These undesirable by-products alter the properties of the compound. The cross-linked silicone molecule can cause gellation of the product. The vitamin cross-linked to another vitamin lacks water solubility and therefore results in products, which split into two phases. These problems have resulted in lack of commercial success of the products. It was not until the current invention was it understood that the reaction of a silicone methyl ester with the hydroxyl vitamin that clear homogeneous cosmetically acceptable products could be produced that do not split into two phases.

THE INVENTION

Object of the Invention

It is the object of the present invention to provide a series of novel silicone esters, which contain within the molecule an "active" functionality. The selection of the proper methyl ester silicone results in the ability to prepare products, which have solubility in a wide range of solvents and are free of undesired by products encountered in the polyester chemistry disclosed in U.S. Pat. No. 5,210,133.

It is another objective of the current invention to provide a method of treating hair and skin with these esters. The process for treating the hair and skin comprises the contacting of the hair or skin with an effective conditioning amount of the silicone ester. The silicone portion of the molecule is substantive to the substrate, hair, and skin and binds there. The beneficial effect of the active is enhanced since the silicone delivers the active to the surface of the hair or skin. This prolonged intimate contact allows for enhanced performance by the active.

It is still another objective of the current invention to provide a product, which conditions, remoisturizes and softens skin but does has a marked reduction in the irritation to the skin of lanolin or cholesterol. The incorporated of the active into the polyester results in the minimization or elimination of irritation to eye and skin.

SUMMARY OF THE INVENTION

The present invention relates to a series of novel silicone ester compounds. The compounds by virtue of the Vitamin A, Vitamin A-2, and Vitamin E, offer outstanding antioxidant properties when applied to the skin additionally provide refatting, moisturization, conditioning and softening.

The ester compounds of the invention are prepared by the esterification of a very specific silicone methyl ester directly with a hydroxyl vitamin, producing a silicone alkyl ester heretofore unknown in the art.

it will be clearly understood that the silicone compounds may contain one or many a hydroxyl groups, ad the active the lanolin and or cholesterol contains only one hydroxyl group. This means that the preparation of the compounds of the present invention differ in another substantial and unexpected way from the compounds of U.S. Pat. No. 5,3210,133 to O'Lenick Jr, issued May 1993. The '133 patent is made by reacting a diacid with a silicone compound containing a hydroxyl group and a vitamin containing a hydroxyl group. In addition to the problem already described wherein with the both sides of the diacid react with two different silicone molecules or different two vitamin molecules, producing upwards of 45% undesired insoluble materials, there is a problem when there is more than one hydroxyl group present in the silicone molecule. The '133 patent discloses a situation wherein there are multiple hydroxyl groups on silicone. In this case, a crosslinking of the diacid and multi-hydroxyl silicone occurs forming an insoluble gel. The compounds of the present invention overcome this problem, since no diacid is used.

DETAILED DESCRIPTION OF THE INVENTION

As stated the ester compounds of the invention by are prepared by the reaction, a methyl undecylenate substituted silicone with a hydroxyl vitamin. The methyl undecylenate silicone may optionally contain alkyl groups, and/or alkoxy groups.

Reactant Silicones useful in the reparation of the compounds of the present invention conform to the following structure:

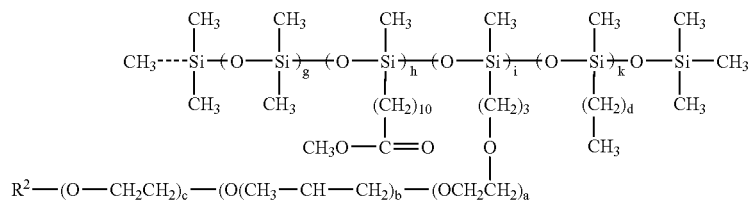

and are reacted with hydroxyl vitamins $R^1$-OH to produce the compounds of the present invention:

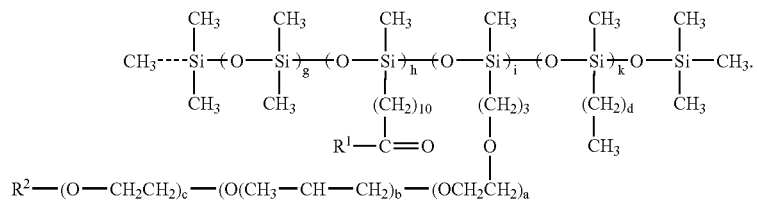

wherein:
a, b and c are independently integers ranging from 0 to 20;
d is an integer ranging from 5 to 33.
g is an integer ranging from 0 to 1,000
h is an integer ranging from 1 to 20;
i is an integer ranging from 0 to 20;
k is an integer ranging from 0 to 20;
$R^1$ is selected from the group consisting of

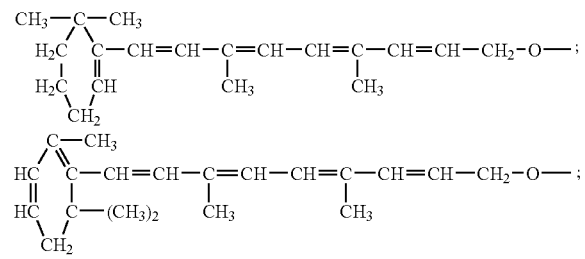

and

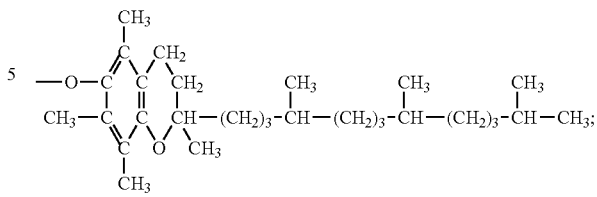

$R^2$ is H or $CH_3$.

The hydroxyl functional actives all are part of a class of natural products, which can be collectively called actives, since they have a beneficial effect when applied to the hair or skin.

Hydroxy-vitamin Examples

Example A—Vitamin A

Vitamin A is 3,7 dimethyl-9-(2,6,6-trimethyl-1-cyclohexen-1-yl)-2,4,6,8-nontetraen-1-ol. It is a well-known commercially available material. The structure of
$R^1$ is:

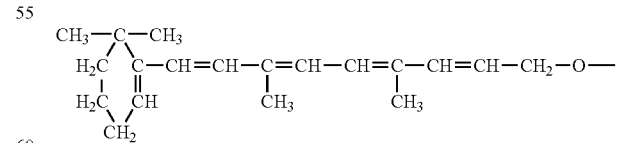

Example B—Vitamin A-2

Vitamin A-2 is 3,4 didehydroretinol. It is a well-known commercially available material.

The structure of $R^1$ is:

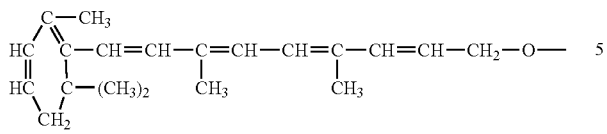

Example C—Vitamin E

Vitamin E is 2,5,7,8-tetramethyl-2-(4',8',12'-trimethyl tridecyl)-6 chromanol also called alpha tocopherol. It is a naturally occurring vitamin. It is a well-known commercially available material. $R^1$ is:

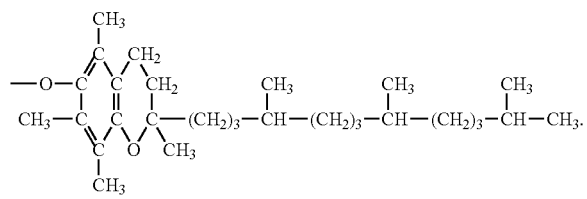

All these hydroxyl active materials are well known and the structures are documented in many textbooks. One reference book is the Merck Index Eleventh Edition published in 1989.

PREFERRED EMBODIMENT

In a preferred embodiment $R^1$ is

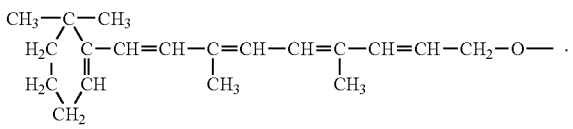

In a preferred embodiment $R^1$ is

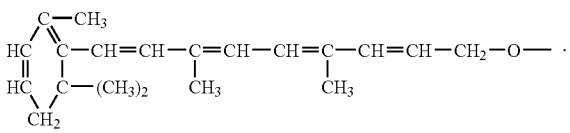

In a preferred embodiment $R^1$ is

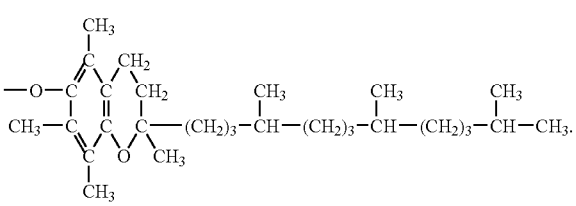

In a preferred embodiment, $R^1$ is i and k are each 0.
In a preferred embodiment, $R^1$ is i is 0.
In a preferred embodiment, $R^1$ is k is 0.
In a preferred embodiment $R^1$ is i and k range between 1 and 20.

EXAMPLES SILICONE COMPONENT

The silicone components of the present invention are all available form Siltech LLC Dacula Ga. They are items of commerce prepared by methods known to those skilled in the art.

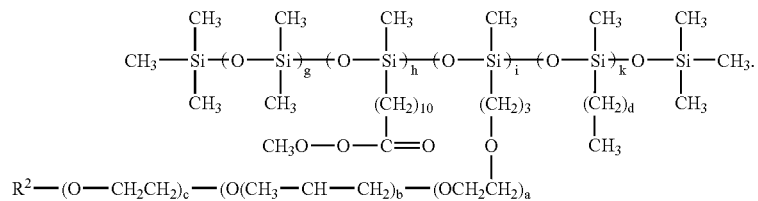

wherein;
a, b and c are independently integers ranging from 0 to 20;
d is an integer ranging from 5 to 33;
g is an integer ranging from 0 to 1,000
h is an integer ranging from 1 to 20;
i is an integer ranging from 0 to 20;
k is an integer ranging from 0 to 20.

Class 1

(In this class the values of both i and k are each 0, therefore a, b, c, d, e, f are not present)

Examples 1–7

| Example | g | h |
|---|---|---|
| 1 | 0 | 1 |
| 2 | 25 | 5 |
| 3 | 50 | 5 |
| 4 | 75 | 10 |
| 5 | 250 | 10 |
| 6 | 500 | 15 |
| 7 | 1000 | 20 |

Class 2 (In this class the value of k is 0)

Examples 8–14

| Example | g | h | i | a | b | c | $R^2$ |
|---|---|---|---|---|---|---|---|
| 8 | 0 | 1 | 1 | 0 | 0 | 0 | H |
| 9 | 25 | 5 | 5 | 5 | 5 | 5 | H |
| 10 | 50 | 5 | 5 | 10 | 2 | 0 | $CH_3$ |
| 11 | 75 | 10 | 10 | 0 | 0 | 0 | $CH_3$ |
| 12 | 250 | 10 | 10 | 10 | 10 | 10 | H |
| 13 | 500 | 15 | 15 | 10 | 10 | 10 | $CH_3$ |
| 14 | 1000 | 20 | 20 | 20 | 20 | 20 | H |

Class 3 (In this class the value of i is 0.)

Examples 9–21

| Example | g | h | k | d |
|---|---|---|---|---|
| 15 | 0 | 1 | 1 | 5 |
| 16 | 25 | 5 | 10 | 9 |
| 17 | 50 | 5 | 10 | 17 |
| 18 | 75 | 10 | 5 | 17 |
| 19 | 250 | 10 | 5 | 11 |
| 20 | 500 | 15 | 20 | 33 |
| 21 | 1000 | 20 | 15 | 11 |

Class 4
(In this class the value of k and i are at least 1, therefore all elements are present)

Examples 22–28

| Example | g | h | i | k | a | b | c | $R^2$ | d |
|---|---|---|---|---|---|---|---|---|---|
| 22 | 0 | 1 | 1 | 20 | 0 | 0 | 0 | H | 11 |
| 23 | 25 | 5 | 10 | 5 | 10 | 10 | 10 | $CH_3$ | 9 |
| 24 | 50 | 5 | 5 | 1 | 2 | 2 | 2 | H | 33 |
| 25 | 75 | 10 | 10 | 4 | 5 | 10 | 5 | H | 11 |
| 26 | 250 | 10 | 5 | 10 | 20 | 20 | 20 | $CH_3$ | 11 |
| 27 | 500 | 15 | 20 | 10 | 5 | 10 | 10 | H | 33 |
| 28 | 1000 | 20 | 15 | 20 | 5 | 1 | 5 | $CH_3$ | 11 |

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240° C. under an inert nitrogen blanket. The nitrogen blanket preserves the color. Preferred temperature range is between 150 and 200° C. Water is removed from the reaction, which is done using a nitrogen sparge or vacuum.

Example 29

Into a suitable round bottom, three neck flash equipped with a Dean Stark trap, a thermometer and a nitrogen sparge is added 494.0 grams of silicone compound (example 1), 0.25% by weight of the total batch charged of stannous oxylate and 286.0 grams of Vitamin example A. The reaction mass is blanketed with nitrogen, and heated to 180 and 200° C. Once the reaction temperature reaches 150° C. water begins to boil off and is collected in the Dean Stark Trap. Within four to five hours, the theoretical water is collected off and the acid value is very low. The product is used without additional purification.

Example 30–57

Example 29 is repeated only this time the specified amount of the specified silicone reactant is substituted for the silicone example 1, and the specified amount of the specified vitamin is substituted for the Vitamin Example A. The same reaction procedure is followed.

| | Silicone Compound | | Vitamin Compound | |
|---|---|---|---|---|
| Example | Example | Grams | Example | Grams |
| 30 | 2 | 675.2 | A | 286.0 |
| 31 | 3 | 1045.2 | B | 284.0 |
| 32 | 4 | 836.6 | C | 431.0 |
| 33 | 5 | 2131.6 | A | 286.0 |
| 34 | 6 | 2740.0 | B | 284.0 |
| 35 | 7 | 3970.0 | C | 431.0 |
| 36 | 8 | 422.0 | A | 286.0 |
| 37 | 9 | 1536.8 | B | 284.0 |
| 38 | 10 | 1703.6 | C | 431.0 |
| 39 | 11 | 832.2 | A | 286.0 |
| 40 | 12 | 3730.4 | B | 284.0 |
| 41 | 13 | 4295.0 | A | 286.0 |
| 42 | 14 | 7032.0 | C | 431.0 |
| 43 | 15 | 865.0 | B | 284.0 |
| 44 | 16 | 820.6 | C | 431.0 |
| 45 | 17 | 1333.3 | A | 286.0 |
| 46 | 18 | 980.5 | B | 284.0 |
| 47 | 19 | 222.1 | C | 431.0 |
| 48 | 20 | 2931.0 | A | 286.0 |
| 49 | 21 | 4015.0 | B | 284.0 |
| 50 | 22 | 1401.0 | C | 431.0 |
| 51 | 23 | 4038.6 | A | 286.0 |
| 52 | 24 | 1968.0 | A | 286.0 |
| 53 | 25 | 2049.0 | B | 284.0 |
| 54 | 26 | 3977.0 | C | 431.0 |
| 55 | 27 | 4667.0 | A | 286.0 |
| 56 | 28 | 4414.0 | B | 284.0 |

Applications Examples

The compounds of the present invention are applied to the skin in a variety of formulations. The proper selection of the correct vitamin results in optimizing the antioxidant/anti-free radical protection.

Optimization of the silicone polymer results in optimizing the solubility of the material.

Using class 1 silicone reactants, since the values of both i and k are each 0, the resulting antioxidant activity is seen in a silicone soluble product. There is neither alkoxy (water-soluble) nor alkyl (fatty soluble) groups.

Using class 2 silicones, water solubilizing groups have been introduced. This results in products having a better partition coefficient in aqueous phases, and consequently delivery of the antioxidant protecting properties is improved from the aqueous phase.

Using Class 3 silicones, the solubility in fatty oils is increased. This allows for delivery of antioxidant properties from fatty oils, esters and other mineral oil soluble systems.

Finally, Using Class 4 silicones, there are groups rendering solubility in silicone oil, mineral oil and water. This allows for delivery of antioxidant properties a variety of phases, since the compounds will partition in all phases.

As can be readily seen, the compounds of the present invention allow a wide degree of formulation latitude for making personal care products.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

IN THE SPECIFICATIONS

Reactant Silicones useful in the reparation of the compounds of the present invention conform to the following structure;

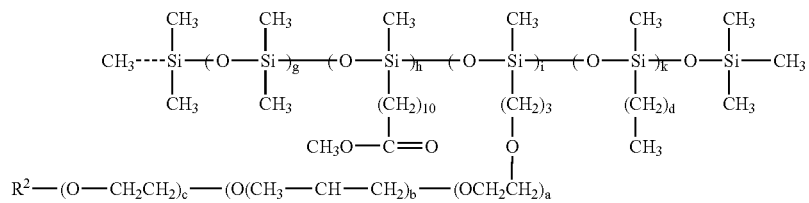

and are reacted with hydroxyl vitamins $R^1$-OH to produce the compounds of the present invention:

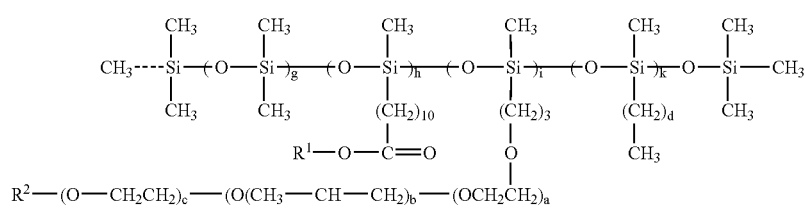

The invention claimed is:

1. A silicone vitamin ester conforming to the following structure;

wherein:
a, b and c are independently integers ranging from 0 to 20;
d is an integer ranging from 5 to 33.
g is an integer ranging from 0 to 1,000
h is an integer ranging from 1 to 20;
i is an integer ranging from 0 to 20;
k is an integer ranging from 0 to 20;
$R^1$ is selected from the group consisting of

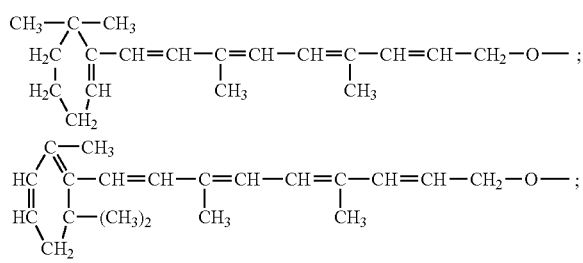

and

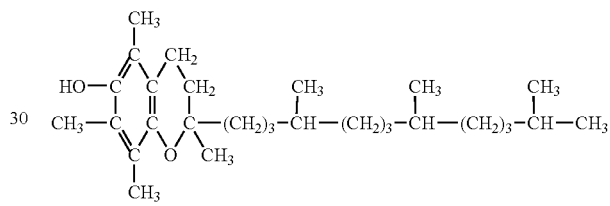

$R^2$ is H or $CH_3$.

[Structural formula of silicone compound with terminal groups including $(CH_3)_3Si$-$(OSi(CH_3)_2)_g$-$(OSi(CH_3)((CH_2)_{10}C(=O)R^1))_h$-$(OSi(CH_3)((CH_2)_3O-(OCH_2CH_2)_a-(O(CH_3)CHCH_2)_b-(OCH_2CH_2)_c-R^2))_i$-$(OSi(CH_3)((CH_2)_dCH_3))_k$-$OSi(CH_3)_3$]

wherein;
 a, b and c are independently integers ranging from 0 to 20;
 d is an integer ranging from 5 to 33;
 f is an integer ranging from 2 to 12;
 g is an integer ranging from 0 to 1,000;
 h is an integer ranging from 1 to 20;
 i is an integer ranging from 0 to 20;
 k is an integer ranging from 0 to 20;
 $R^1$ is selected from the group consisting of

[Structure 1: cyclic structure with $CH_3$-$C(CH_3)$-$CH_2$-$CH_2$-$CH_2$-$CH$ ring attached to -C=CH-CH=C(CH_3)-CH=CH-C(CH_3)=CH-CH_2-O-];

[Structure 2: aromatic-like ring with $CH$=$CH$, $C(CH_3)_2$, $CH_2$ attached to -C-CH=CH-C(CH_3)=CH-CH=C(CH_3)-CH=CH-CH_2-O-];

and

[Structure 3: cyclic ring structure -O-C=C(CH_3)-C(CH_2)(CH_2)-C(CH_3)(O)- with chain -(CH_2)_3-CH(CH_3)-(CH_2)_3-CH(CH_3)-(CH_2)_3-CH(CH_3)-CH_3];

$R^2$ is H or $CH_3$.

2. A silicone ester of claim 1 wherein $R^1$ is

[Structure showing cyclic ring with CH_3-C(CH_3), H_2C, H_2C, CH, CH_2 attached to -C=CH-CH=C(CH_3)-CH=C(CH_3)-CH=CH-CH_2-O-].

3. A silicone ester of claim 1 wherein $R^1$ is

[Structure showing cyclic ring HC=C(CH_3), HC, CH_2, with C-(CH_3)_2 attached to -C-CH=CH-C(CH_3)=CH-CH=C(CH_3)-CH=CH-CH_2-O-].

4. A silicone ester of claim 1 wherein $R^1$ is

[Structure showing -O-C=C(CH_3)-C(CH_2)(CH_2)-C(CH_3)(O-CH_3)- attached to -(CH_2)_3-CH(CH_3)-(CH_2)_3-CH(CH_3)-(CH_2)_3-CH(CH_3)-CH_3].

5. A silicone ester of claim 2 wherein i and k are each 0.

6. A silicone ester of claim 2 wherein i is 0.

7. A silicone ester of claim 2 wherein k is 0.

8. A silicone ester of claim 2 wherein i and k range between 1 and 20.

9. A silicone ester of claim 3 wherein i and k are each 0.

10. A silicone ester of claim 3 wherein i is 0.

11. A silicone ester of claim 3 wherein k is 0.

12. A silicone ester of claim 3 wherein i and k range between 1 and 20.

13. A silicone ester of claim 4 wherein i and k are each 0.

14. A silicone ester of claim 4 wherein i is 0.

15. A silicone ester of claim 4 wherein k is 0.

16. A silicone ester of claim 4 wherein i and k range between 1 and 20.

* * * * *